United States Patent
Tourrette et al.

(10) Patent No.: US 7,901,414 B2
(45) Date of Patent: Mar. 8, 2011

(54) CASSETTE AND INJECTOR FOR FLEXIBLE INTRAOCULAR LENS AND METHOD FOR INJECTING SUCH LENSES

(75) Inventors: Philippe Tourrette, La Jarrie (FR); Pascal Bernard, Lagord (FR); Vincent Raquin, La Rochelle (FR)

(73) Assignee: Ioltechnologie-Production, Perigny (FR)

( * ) Notice: Subject to any disclaimer, the term of this patent is extended or adjusted under 35 U.S.C. 154(b) by 850 days.

(21) Appl. No.: 10/498,492

(22) PCT Filed: Dec. 12, 2002

(86) PCT No.: PCT/FR02/04329
§ 371 (c)(1),
(2), (4) Date: Jan. 31, 2005

(87) PCT Pub. No.: WO03/049645
PCT Pub. Date: Jun. 19, 2003

(65) Prior Publication Data
US 2005/0125000 A1 Jun. 9, 2005

(30) Foreign Application Priority Data
Dec. 12, 2001 (FR) ..................... 01 16040

(51) Int. Cl.
*A61F 9/00* (2006.01)
(52) U.S. Cl. ...................................... 606/107
(58) Field of Classification Search .............. 606/107
See application file for complete search history.

(56) References Cited

U.S. PATENT DOCUMENTS

| 4,423,809 | A | | 1/1984 | Mazzocco |
|---|---|---|---|---|
| 4,573,998 | A | | 3/1986 | Mazzocco |
| 4,702,244 | A | | 10/1987 | Mazzocco |
| 4,715,373 | A | | 12/1987 | Mazzocco et al. |
| 4,750,498 | A | | 6/1988 | Graham |
| 4,834,094 | A | | 5/1989 | Patton et al. |
| 5,190,553 | A | | 3/1993 | Kanert et al. |
| 5,275,604 | A | | 1/1994 | Rheinish et al. |
| 5,304,182 | A | | 4/1994 | Rheinish et al. |
| 5,494,484 | A | | 2/1996 | Feingold |
| 5,496,328 | A | | 3/1996 | Nakajima et al. |
| 5,499,987 | A | | 3/1996 | Feingold |
| 5,582,614 | A | | 12/1996 | Feingold |
| 5,616,148 | A | | 4/1997 | Eagles et al. |
| 5,620,450 | A | * | 4/1997 | Eagles et al. .................. 606/107 |
| 5,728,102 | A | | 3/1998 | Feingold et al. |

(Continued)

FOREIGN PATENT DOCUMENTS

AU 710419 9/1999

(Continued)

*Primary Examiner* — Todd E Manahan
*Assistant Examiner* — Eric Blatt
(74) *Attorney, Agent, or Firm* — Young & Thompson (57) ABSTRACT

A lens cassette for a lens injector includes a tubular body and a piston mobile in the tubular body to move forward a lens towards an injection cannula. The device includes a housing (30, 31) for an intraocular lens (10), an inserting zone (33) for the piston, and outlet zone (35) for the lens and its own closure element (25, 26) for enclosing the lens. The cassette is made of a material enabling sterilization of the lens enclosed in the cassette, while providing a prolonged shelf life. The cassette assembly with the lens and the injector can be sterilized in a sealed flask by gamma radiation.

33 Claims, 4 Drawing Sheets

U.S. PATENT DOCUMENTS

| Patent | Date | Inventor(s) | |
|---|---|---|---|
| 5,772,666 A | 6/1998 | Feingold et al. | |
| 5,800,442 A | 9/1998 | Wolf et al. | |
| 5,807,400 A * | 9/1998 | Chambers et al. | 606/107 |
| 5,810,833 A | 9/1998 | Brady et al. | |
| 5,860,984 A | 1/1999 | Chambers et al. | |
| 5,868,751 A | 2/1999 | Feingold | |
| 5,873,879 A | 2/1999 | Figueroa et al. | |
| 5,876,406 A | 3/1999 | Wolf et al. | |
| 5,876,440 A | 3/1999 | Feingold | |
| 5,902,307 A * | 5/1999 | Feingold et al. | 606/107 |
| 5,928,245 A | 7/1999 | Wolf et al. | |
| 5,941,886 A | 8/1999 | Feingold | |
| 5,947,975 A | 9/1999 | Kikuchi et al. | |
| 5,947,976 A | 9/1999 | Van Noy et al. | |
| 6,001,107 A | 12/1999 | Feingold | |
| 6,010,510 A | 1/2000 | Brown et al. | |
| 6,048,348 A | 4/2000 | Chambers et al. | |
| 6,056,757 A | 5/2000 | Feingold et al. | |
| 6,074,397 A | 6/2000 | Chambers et al. | |
| 6,083,231 A | 7/2000 | Van Noy et al. | |
| 6,142,999 A | 11/2000 | Brady et al. | |
| 6,143,000 A | 11/2000 | Feingold | |
| 6,162,229 A | 12/2000 | Feingold et al. | |
| 6,174,315 B1 | 1/2001 | Chambers et al. | |
| 6,241,737 B1 | 6/2001 | Feingold | |
| RE37,387 E | 9/2001 | Brady et al. | |
| 6,312,433 B1 | 11/2001 | Butts et al. | |
| 6,336,932 B1 | 1/2002 | Figueroa et al. | |
| 6,355,046 B2 | 3/2002 | Kikuchi et al. | |
| 6,371,960 B2 | 4/2002 | Heyman et al. | |
| 6,387,101 B2 | 5/2002 | Butts et al. | |
| 6,398,789 B1 | 6/2002 | Capetan | |
| 6,406,481 B2 | 6/2002 | Feingold et al. | |
| 6,468,282 B2 | 10/2002 | Kikuchi et al. | |
| 6,506,195 B2 | 1/2003 | Chambers et al. | |
| 6,629,979 B1 | 10/2003 | Feingold et al. | |
| 6,685,740 B2 | 2/2004 | Figueroa et al. | |
| 6,695,988 B1 * | 2/2004 | Schlagel et al. | 264/2.6 |
| 6,712,848 B1 | 3/2004 | Wolf et al. | |
| 6,921,405 B2 | 7/2005 | Feingold et al. | |
| 7,025,782 B2 | 4/2006 | Kobayashi et al. | |
| 7,037,312 B2 | 5/2006 | Kikuchi et al. | |
| 7,223,287 B2 | 5/2007 | Jeannin et al. | |
| 7,226,455 B2 | 6/2007 | Jeannin et al. | |
| 2001/0001822 A1 | 5/2001 | Chambers et al. | |
| 2001/0007942 A1 | 7/2001 | Kikuchi et al. | |
| 2001/0014808 A1 | 8/2001 | Kikuchi et al. | |
| 2001/0041897 A1 | 11/2001 | Feingold et al. | |
| 2002/0077633 A1 | 6/2002 | Kikuchi et al. | |
| 2002/0082609 A1* | 6/2002 | Green | 606/107 |
| 2002/0151904 A1 | 10/2002 | Feingold et al. | |
| 2003/0036765 A1* | 2/2003 | Van Noy | 606/107 |
| 2003/0187455 A1 | 10/2003 | Kobayashi et al. | |
| 2004/0117012 A1 | 6/2004 | Vincent | |
| 2004/0127911 A1 | 7/2004 | Figueroa et al. | |
| 2004/0193263 A1 | 9/2004 | Bryan | |
| 2005/0049605 A1 | 3/2005 | Vaquero et al. | |
| 2005/0049606 A1 | 3/2005 | Vaquero et al. | |
| 2005/0065534 A1 | 3/2005 | Hohl | |
| 2005/0125000 A1 | 6/2005 | Tourrette et al. | |
| 2005/0125059 A1 | 6/2005 | Pinchuk et al. | |
| 2005/0149058 A1 | 7/2005 | Lin et al. | |
| 2005/0222579 A1 | 10/2005 | Vaquero et al. | |
| 2005/0261703 A1 | 11/2005 | Feingold et al. | |
| 2006/0036262 A1 | 2/2006 | Hohl | |
| 2006/0085013 A1 | 4/2006 | Dusek et al. | |
| 2006/0122700 A1 | 6/2006 | Kurosaka et al. | |
| 2006/0142780 A1 | 6/2006 | Pynson et al. | |
| 2006/0142781 A1 | 6/2006 | Pynson et al. | |
| 2006/0167466 A1 | 7/2006 | Dusek | |
| 2006/0293694 A1 | 12/2006 | Futamura | |

FOREIGN PATENT DOCUMENTS

| | | |
|---|---|---|
| AU | 751178 | 8/2002 |
| CA | 2173609 | 2/1996 |
| CA | 2183451 | 8/1996 |
| CA | 2333104 | 11/1999 |
| CA | 2234002 | 4/2005 |
| CA | 2565395 | 11/2005 |
| CN | 1146142 | 3/1997 |
| CN | 1172421 | 2/1998 |
| EP | 0519282 | 12/1992 |
| EP | 0503136 | 3/1996 |
| EP | 0722292 | 7/1996 |
| EP | 1079888 | 3/2001 |
| EP | 0980230 | 1/2002 |
| EP | 0723429 | 4/2002 |
| EP | 0688183 | 10/2002 |
| EP | 1290990 | 3/2003 |
| EP | 0901343 | 8/2003 |
| EP | 0962195 | 8/2003 |
| EP | 1338254 | 8/2003 |
| EP | 1023880 | 10/2003 |
| EP | 1360946 | 11/2003 |
| EP | 1360947 | 11/2003 |
| EP | 1037573 | 9/2004 |
| EP | 0813400 | 11/2004 |
| EP | 1282384 | 12/2004 |
| EP | 0746237 | 9/2005 |
| EP | 0858304 | 10/2005 |
| EP | 0804131 | 12/2005 |
| EP | 1356791 | 4/2006 |
| EP | 1649831 | 4/2006 |
| EP | 1287792 | 5/2006 |
| EP | 1320338 | 5/2006 |
| EP | 1360945 | 11/2006 |
| EP | 1481652 | 11/2006 |
| JP | 5103803 | 4/1993 |
| JP | 5103808 | 4/1993 |
| JP | 5103809 | 4/1993 |
| JP | 7023990 | 1/1995 |
| JP | 8019558 | 1/1996 |
| JP | 8024282 | 1/1996 |
| JP | 2000/210312 | 8/2000 |
| JP | 2001/104363 | 4/2001 |
| JP | 2001/340374 | 12/2001 |
| JP | 2003/070830 | 3/2003 |
| JP | 2003/325570 | 11/2003 |
| JP | 2004/290690 | 10/2004 |
| WO | WO9407436 | 4/1994 |
| WO | WO9529648 | 11/1995 |
| WO | 96/03924 | 2/1996 |
| WO | WO9603924 | 2/1996 |
| WO | WO9801089 | 1/1998 |
| WO | WO9959668 | 11/1999 |
| WO | WO00/49974 | 8/2000 |
| WO | WO00/62712 | 10/2000 |
| WO | WO02/058596 | 8/2002 |
| WO | WO02/074202 | 9/2002 |
| WO | WO03/015657 | 2/2003 |
| WO | WO03/049645 | 6/2003 |
| WO | WO03/077805 | 9/2003 |
| WO | WO2004/089251 | 10/2004 |
| WO | WO2004/091447 | 10/2004 |
| WO | WO2004/105649 | 12/2004 |
| WO | WO2004/108018 | 12/2004 |
| WO | WO2005/023154 | 3/2005 |
| WO | WO2005/030097 | 4/2005 |
| WO | WO2005/070341 | 8/2005 |
| WO | WO2005/084588 | 9/2005 |
| WO | WO2006/006213 | 1/2006 |
| WO | WO2006/070561 | 7/2006 |
| WO | WO2006/071561 | 7/2006 |
| WO | WO2006/071597 | 7/2006 |
| WO | WO2006/080191 | 8/2006 |

* cited by examiner

CASSETTE AND INJECTOR FOR FLEXIBLE INTRAOCULAR LENS AND METHOD FOR INJECTING SUCH LENSES

The present invention relates to the packaging and injection of intraocular lenses (IOLs) and relates more particularly to intraocular lenses made from flexible material.

An intraocular lens, also known as an intraocular implant, has an optic part for correcting ametropia and a haptic part that supports the optic part in the required location in the eye, which may be the anterior chamber or the posterior chamber, to replace a natural lens affected by cataract or to provide a correction with an intact natural lens.

The first intraocular implants had the optic part made of rigid material, and in particular PMMA, which requires a large incision corresponding at least to the diameter of the optic part, i.e. at least 6 mm. In the case of intraocular implants made entirely or partly of flexible material, the haptic part may be folded or rolled, more generally deformed, to allow its insertion through a sclerocorneal incision whose length is less than half the diameter of the optic part.

Numerous devices for folding intraocular implants are known in the art. They are often difficult to use and do not reduce the effective width of the optic part to less than half the diameter of the haptic part.

Also known in the art are injectors that roll or fold the optic part at several places, so that the effective width of the optic part is less than half the diameter of the optic part. Moreover, the injector improves control of the insertion of the implant, whether into the anterior chamber or the posterior chamber, and the implant can be injected with one hand.

The implants and the injectors must be sterilized by means appropriate to the materials from which they are made. At present, certain hydrophilic acrylic intraocular implants are sterilized in an aqueous solution by steam sterilization in an autoclave.

At present, other implants, and in particular PMMA, hydrophobic acrylic, silicone, and bimaterial (PMMA and hydrophobic acrylic) lenses, are sterilized with ethylene oxide (ETO). Others, and in particular bimaterial (PMMA and hydrophilic acrylic) implants, must be sterilized by irradiation with gamma rays.

Prior to steam sterilization in an autoclave, the intraocular implant is placed in a flask containing an aqueous saline solution and which is then sealed hermetically before it is placed in the autoclave. The flask serves as container or packaging for the implant.

The same applies to sterilization by gamma radiation, i.e. the intraocular implant is placed in a flask containing an aqueous solution which is hermetically sealed before undergoing irradiation.

Finally, hydrophobic acrylic and bimaterial (PMMA and hydrophilic acrylic) or silicone implants are sterilized dry in a container that is permeable to ethylene oxide and then packaged dry in a container of appropriate shape.

The injectors are usually made of polypropylene or low-density polyethylene. The components of the injectors made from these materials are sterilized with ethylene oxide in a blister pack with a film permeable to ETO and independent of the container used for the intraocular implant itself.

At the moment of use, the injector is removed from its packaging and the intraocular implant is then extracted from its flask or other container to be loaded into the injector. This operation complicates the use of the injectors and constitutes an additional risk to the integrity of the implant, in particular if transferred from the packaging to an injector loading area by means of forceps.

WO/96/03924 describes a device for inserting flexible intraocular lenses utilizing an integral compartment of the body of the injector as a packaging device for transporting and storing the lens in a suspended and stress-free state. In one embodiment, a first part of the compartment is formed in one piece with the tubular body and a second part is simply placed on the first part. This kind of compartment cannot be used as a packaging device in itself. For this purpose, a canula is fitted around the compartment and attached to the body of the piston of the injector. In a different embodiment the compartment is integral with the canula.

The same applies to the intraocular lenses of the published Japanese patent applications JP-2001104363, JP-2001104347, JP-2001340374, which are simply placed between two members that cannot constitute packaging suitable for sterilization.

If the implant is made from silicone or hydrophobic acrylic, the combination of the implant, the body of the injector, and the canula attached to the injector may be sterilized with ETO. However, this kind of combination has a limited shelf life (approximately six months). This is because the canula contains, beneath the interior wall, a lubricant such as glycerol stearate, derivatives of polyamide, fatty alcohol polyethoxyethers, polyol ester, or ethoxylated amines, co-molded with the material from which the canula is made. After a limited time, the lubricant that initially impregnated the material of the canula migrates onto the surface of the interior wall of the canula in quantities such that the implant is covered with lubricant on passing through the canula, which affects its transparency and introduces lubricant residues into the eye.

In the case of a hydrophilic acrylic or bimaterial implant, the implant and the combination of the injector body and the canula, or the canula only, may not be sterilized with the packaging, which is typically made of polypropylene, since the canula may not be sterilized at high temperature in an autoclave and this kind of implant may not be sterilized with ETO.

The object of the present invention is to solve the problems of flexible intraocular implant packaging and injection devices, allowing sterilization and/or long-term storage of the implant and easier loading of the implant into an injector.

In a first aspect, the invention provides an intraocular lens cassette for lens injector, of the type comprising a tubular body and a piston mobile in the tubular body to advance a lens toward an injection canula, the cassette being conformed to be loaded into the tubular body and comprising a housing for an intraocular lens, an entry region for the piston, and an exit region for the implant, characterized in that the cassette constitutes packaging for sterilizing the intraocular lens and has its own closure means for enclosing the lens.

A cassette of this kind also constitutes packaging for long-term storage of the implant. This is because it may be made from a material whose sterilization is compatible with that of the intraocular lens, regardless of the material from which the implant is made. The body of the injector and the canula may be made from a material different from that of the cassette, and sterilized and packaged in accordance with a protocol different from that for the cassette and the implant.

In a preferred embodiment, the cassette includes a first member or shell mounted on a second member or shell and mobile between an open position and a closed position, enabling the user to open the cassette to check the intraocular lens, if necessary, or even to take it out to implant it without injection. To this end, the closure means preferably consist in unlockable clipping means.

In one variant, the closure means consist of means for permanent closure of the cassette, preventing access to the implant except by means of the injection device. This kind of cassette can be provided with transparent windows for inspecting the implant before loading it into the injector.

Regardless of the embodiment of the lens (hydrophilic acrylic, bimaterial (hydrophilic/PMMA or hydrophobic/PMMA), silicone, or hydrophobic acrylic), the cassette is preferably made from polyetherimide resin, for example, and may be sterilized by a sterilization method suitable for the material of the implant.

In the case of hydrophilic acrylic intraocular lenses, the cassette may be made from a material that may be sterilized in an autoclave or by irradiation with gamma radiation, for example polyetherimide resin.

In the case of bimaterial intraocular lenses where one material is a hydrophilic flexible material and the other is a rigid material, such as PMMA, the cassette is made from a material that may be sterilized by irradiation with gamma radiation, for example polyetherimide resin.

If the lens is made from silicone or hydrophobic acrylic, the cassette is made from a material that may be sterilized by ETO, for example polyetherimide resin.

According to another aspect of the invention, the cassette and the intraocular lens, on the one hand, and the injector, on the other hand, may be sterilized and packaged in accordance with the same protocol. The cassette enclosing the intraocular lens may even be loaded into the injector and the combination sterilized in accordance with that protocol.

The protocol may theoretically employ sterilization by ETO, but this has certain drawbacks. Firstly, sterilization by ETO implies degassing of the object over a relatively long time period, of the order of two weeks, to achieve an acceptable ethylene oxide level, and, secondly, if the canula of the injector is sterilized by this method, the shelf life is very limited, as already indicated.

However, in accordance with this aspect of the invention, the sterilization protocol employs sterilization by gamma radiation in a wet environment. This is because this type of sterilization may be used for bimaterial intraocular lenses where one material is a hydrophilic flexible material and the other is a rigid material, such as PMMA, or lenses made from a single material, in particular hydrophilic acrylic or PMMA, on the one hand, and a cassette made from resin, in particular polyetherimide, and a polyethylene or polypropylene injector, on the other hand. Surprisingly, it has been found that the injector may be sterilized by gamma radiation with its injection canula having a lubricant on the interior wall without risk of migration of the lubricant on the surface of the interior wall of the canula or risk of contamination of the aqueous solution and of contamination of the intraocular lens by the aqueous solution. The cassette with the intraocular lens and the whole of the injector is sterilized by gamma radiation in a sealed flask, either with the cassette loaded into the injector or with the cassette separate from the injector for subsequent loading.

In another aspect, the invention provides an intraocular implant injector adapted to be loaded with the above kind of cassette on the pathway of a mobile piston and aligned with the canula. The cassette is preferably inserted into the body of the piston by sliding it transversely and clipped in a loading position.

Another aspect of the invention provides a method for the injection of intraocular lenses using an injection device that comprises a tubular body and a mobile piston, which method comprises the following steps: an intraocular lens and a cassette for housing the intraocular lens are prepared, the cassette having a piston entry region and an implant exit region; the intraocular lens and the cassette are sterilized after enclosing the lens in the cassette; the injection device is sterilized; and the closed cassette is inserted into the tubular body of the injector with the piston entry region aligned therewith.

In the case of implants made from hydrophilic acrylic or flexible/rigid bimaterial implants made from hydrophilic flexible acrylic and a rigid material such as PMMA, the implant is preferably introduced into and enclosed in the cassette, introduced into a flask containing an aqueous saline solution, which is then hermetically sealed, the cassette with the implant being sterilized in an autoclave or by gamma radiation.

The injection device is preferably sterilized concomitantly with the cassette and the intraocular lens and in the same flask. The cassette may even be loaded into the injector and then enclosed in the flask containing the aqueous saline solution. Although loading the implant into the cassette before sterilization is greatly preferred, in one variant the implant is not enclosed in the cassette until after sterilization.

If the injector is sterilized with ETO rather than by gamma radiation, the ejection canula may be packaged independently of the tubular body and the piston, to extend the shelf life.

The invention will be better understood and other advantages of the invention will become apparent in the course of the following description, which is given by way of example and with reference to the appended drawings, in which.

Figure 1:
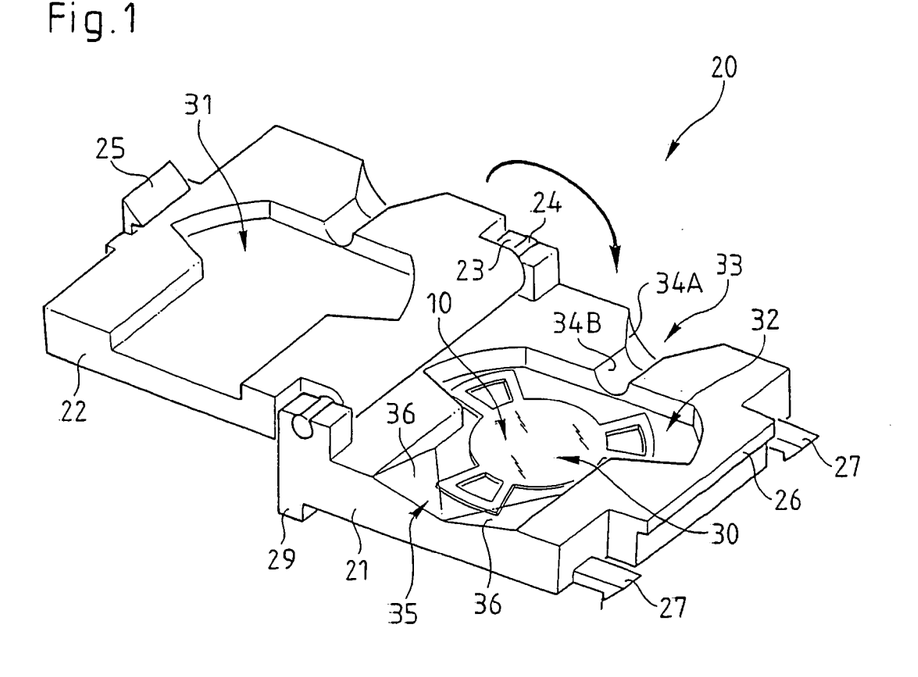
FIG. 1 is a perspective view of a first embodiment of an intraocular lens cassette of the present invention, shown open with an intraocular implant housed in one of its members or shells.
Figure 2:
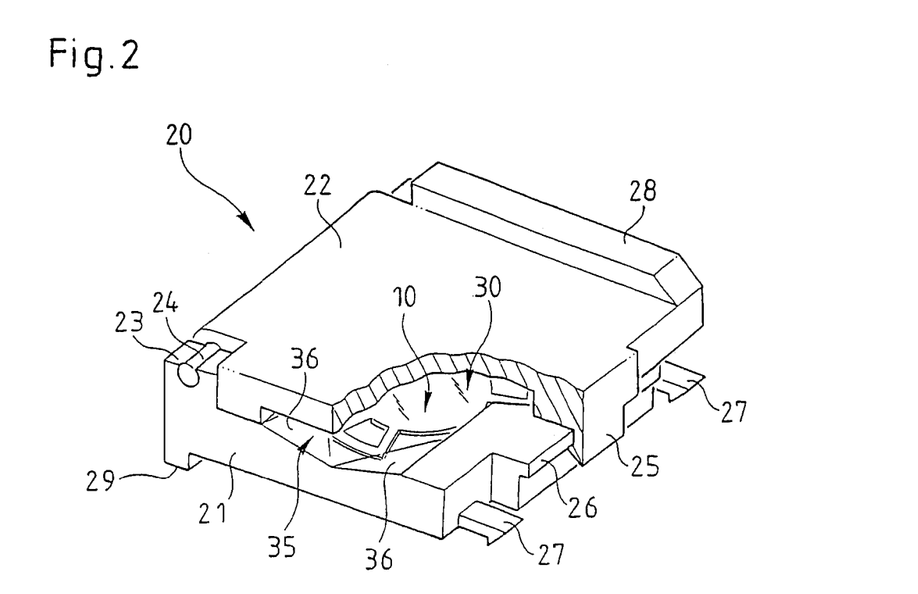
FIG. 2 is a partly cutaway perspective view of the cassette from FIG. 1 when closed.

A cassette 20 according to a first embodiment of the present invention is shown open and closed in FIGS. 1 and 2, respectively. In this embodiment, the cassette comprises a first member or shell 21 that constitutes a base and a second member or shell 22 that constitutes a lid. Each of these members or shells is preferably molded in one piece from plastic material, which is preferably at least partly transparent. Each of the members or shells 21 and 22 has a generally rectangular contour and a thickness that is small in relation to its other dimensions. On either side of the rear of the base is a block comprising an elastically deformable seat 23 adapted to receive a journal 24 of complementary, in particular cylindrical, shape disposed on either side of the rear of the lid and projecting laterally into notches. Assembly is effected by passing the journals through the access slot of the seats 23, the elasticity of the seats retaining the journal for pivoting of the lid.

On the front edge of the lid 22 is a hook 25 that cooperates with a rim 26 at the front of the base 21 when the cassette is closed. The hook 25 is flexed forwards when it encounters the rim 26 and then clips under the rim to lock the cassette. In this embodiment, the cassette closure means are clipping means.

In an embodiment that is not shown, the closure means effect permanent and tamperproof closure of the cassette after insertion of the implant, with the result that the implant may be manipulated only by means of the corresponding injector. In this kind of embodiment, the base and/or the lid are made partly or entirely from a transparent material to allow the implant to be inspected through the transparent wall or walls.

The base 21 and, where applicable, the lid 22 have on the inside face a cavity 30, 31 having a contour and a depth appropriate for accommodating an intraocular lens 10. The housing may be designed to accommodate any intraocular lens configuration, for example that of the embodiment shown in FIG. 9, or designed to accommodate a particular intraocular lens configuration, regardless of the correction effected by the optic part thereof. For an intraocular lens shape of the kind shown, the housing has a configuration substantially complementary to the contour of the implant. The bottom 32 of the cavity is preferably plane, as shown here.

In the embodiment shown in FIG. 1, the cavity 30 of the base 21 defining the housing when the cassette is closed is intended to receive an intraocular lens 10 with three flat haptic parts, with or without apertures, as described in French patent number 2.745.711. To this end, the contour of the cavity 30 is generally T-shaped with the front edge of the lateral arms slightly oblique to retain two of the three flat haptic parts, to prevent any significant movement of the implant. The width of the portion of the cavity that constitutes the stem of the T-shape is slightly greater than the diameter of the optic part of the intraocular lens. The width of the intraocular lens at the level of the two rear lugs disposed in the crossbar portion of the T-shaped cavity is greater than the width of the stem of the T-shape of the cavity in this embodiment. With this kind of configuration, the oblique walls of the crossbar portion of the T-shape cavity at the junction with the walls of the stem of the T-shape of the cavity retain the haptic parts of the intraocular lens to prevent inadvertent escape of the lens from the cassette.

Figure 3:
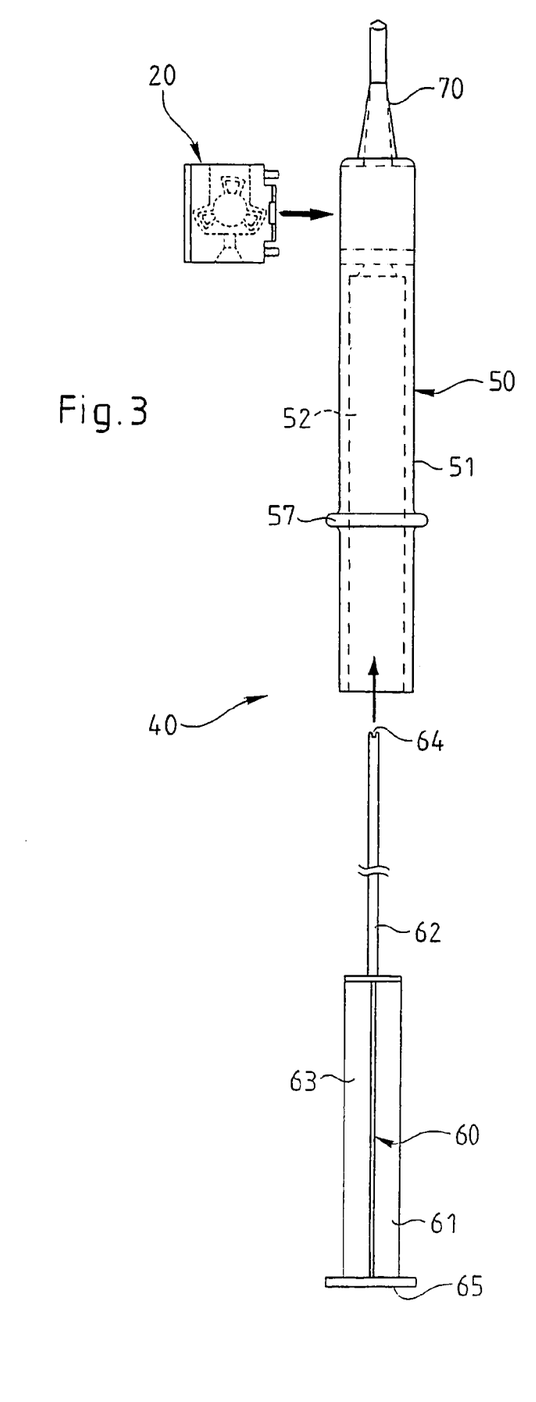
FIG. 3 is a plan view of the cassette from FIGS. 1 and 2, shown to a smaller scale and with an injector, prior to insertion of the cassette and the piston into the tubular body of the injector.
Figure 4:
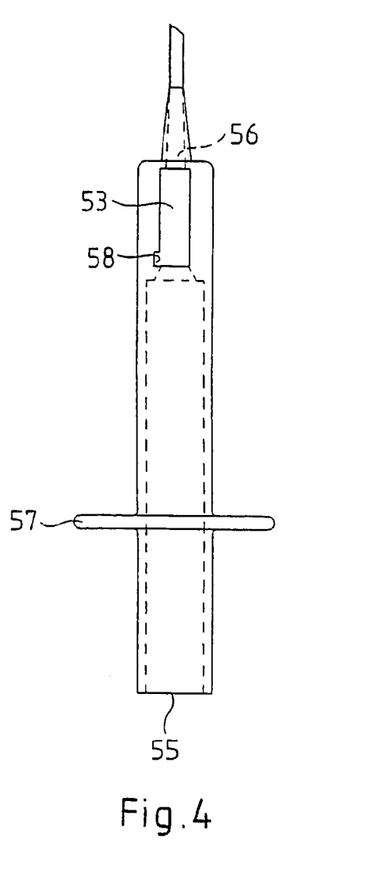
FIG. 4 is a side view of the tubular body of the injector on its own.
Figure 5:
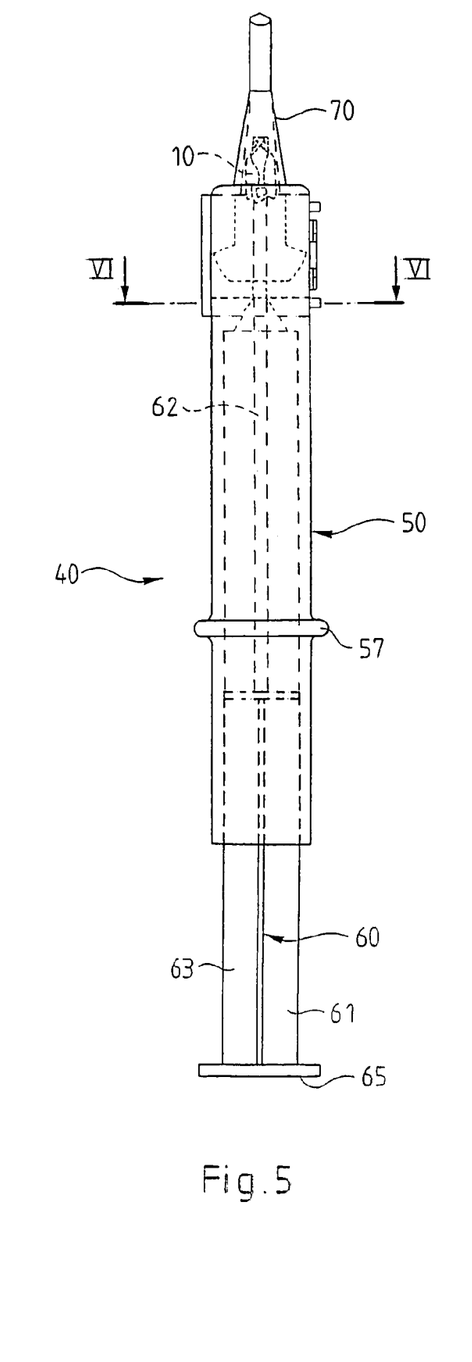
FIG. 5 is a view of the injector during ejection of the implant through the canula.

In this embodiment, the third flat haptic part is on the outlet side 35 of the cavity, in communication with a canula or end-piece 70 (see FIGS. 3 to 5). The cavity 30 includes, as shown here, two oblique triangular flats 36 that constitute a ramp for raising the implant and determining the direction of the rolling that occurs in the canula, as described above.

The entry 33 for the distal end of the plunger 62 of the piston 60 is on the side opposite the exit 35 (FIG. 3). This inlet has a tapered first region 34A followed by a cylindrical second region 34B. The combination of the first and second regions of the base and the lid at the entry of the cassette serve to guide the distal end of the plunger in the cassette.

The lid 22 includes a cavity 31 with the same contour as the cavity 30 in the base and a tapered first region and a semicylindrical second region identical to those of the entry 33. The cavity 31 in the lid has no oblique flats 36. In an embodiment that is not shown, the cavity 31 may have a contour different from that of the cavity 30, or even be dispensed with. In this case, the height of the cavity 30 must be sufficient to allow for the curvature of the implant in a rest state.

Figure 6:
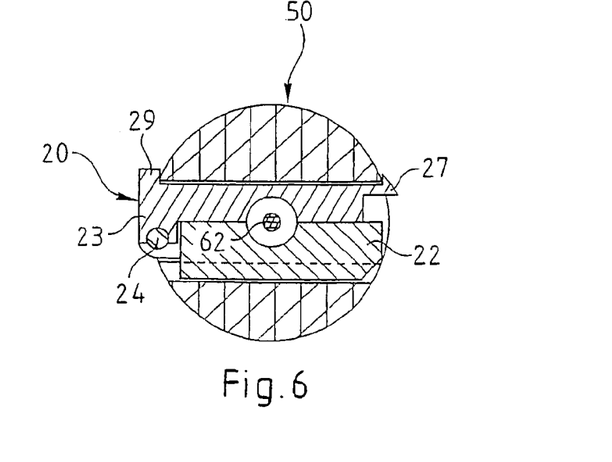
FIG. 6 is a view in section taken along the line VI-VI in FIG. 5 showing the immobilization of the cassette in the tubular body.
Figure 7:
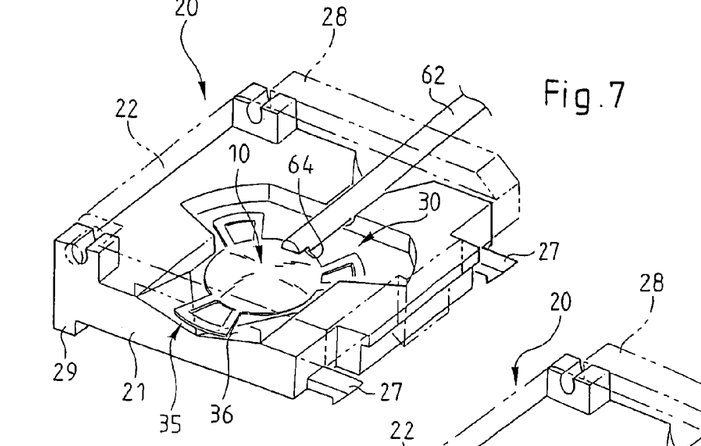
FIG. 7 is a perspective view of the cassette at the start of advancing the implant into the cassette by means of the plunger of the piston.

On the outside of the base 21, at the rear, and aligned with the journals, is a rib 29 that constitutes an abutment to stop sliding movement of the cassette inside the tubular body 40 (see FIG. 6). A pair of hooks 27 in cut-outs on either side of the rim 26 is adapted to cooperate with the exterior surface of the tubular body at the exit from the housing therein, so that when the cassette is inserted into the tubular body the hooks 27 are first deformed and then return to their rest position, in which they cooperate with the rim of the tubular body 50 (see FIG. 6). The hooks 27 constitute clipping means for fixing the cassette into the housing 53 of the tubular body. Similarly, on the exterior of the lid 22, on the entry side, there is a second rib 28 with an oblique front end that cooperates with a complementary groove 58 communicating with the housing 53 in the tubular body, firstly to guide the cassette on insertion into the housing 53 of the tubular body and secondly to constitute polarizing means to prevent incorrect orientation of the cassette in the housing of the tubular body.

For sterilization and subsequent storage, the implant is placed in the cavity 30 and the cassette is closed by the clipping means consisting of the hooks 25 and the rim 26. In the rest state, and in the position shown in FIG. 2, the center of the optic part is in contact with the bottom 32 of the cavity 30. Being an implant with an inward angulation of the order of 10°, the haptic parts inclined at this angle are flattened slightly towards the "bottom" of the cavity 31 in the lid. The total height of the conjoint cavity 30, 31 is preferably slightly greater than the height of the implant along its optic axis, so that there is a small clearance. Similarly, there is an angular clearance allowing slight movement of the haptic members of the implant relative to the contour rim of the cavity.

If the implant is made from a hydrophilic acrylic material, for example a hydroxyethylmethacrylate and methylmethacrylate copolymer, it may be sterilized by steam in autoclave or by gamma radiation. The cassette must be made from a material that may be sterilized by steam either [sic] in an autoclave or by gamma radiation, as appropriate. The cassette is preferably made from ULTEM 1010F polyetherimide from General Electric Company, which may be sterilized by either method.

Figure 8:
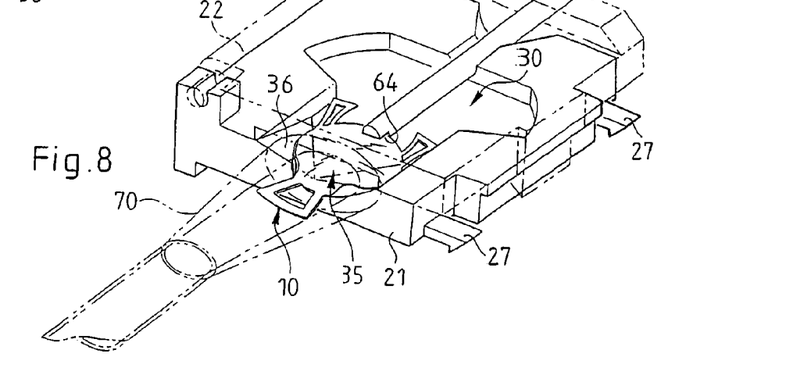
FIG. 8 is analogous to FIG. 7, at the start of entry of the implant into the neck of the canula.
Figure 9:
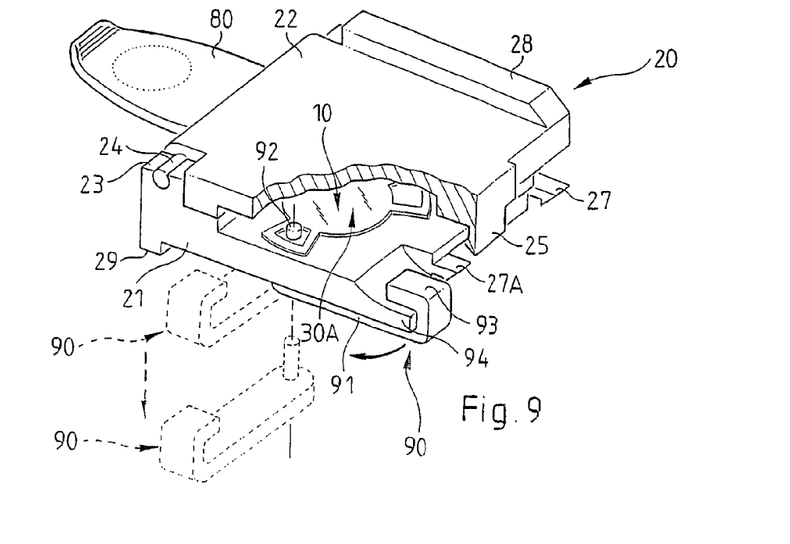
FIG. 9 is a view analogous to that of FIG. 2, for a variant in which the cassette has a holding lug and a removable device for immobilizing the intraocular lens.

FIG. 9 shows a variant of the cassette. The components of this variant are identified by the same reference numbers as those of the same components in FIGS. 1, 2 and 6 to 8.

In this embodiment, the base 21 has at the rear a holding lug 80 extending to the rear and having a raised free edge. This lug facilitates manipulation of the cassette and in particular its insertion into the injection device. This is because it provides a good grip on the cassette until it is nested inside the injection device, as shown in FIG. 6.

In this embodiment, the cavity 30A does not have a T-shaped configuration, with the result that it may be adapted to receive an intraocular lens of any configuration, and in particular with flat haptic members with other shapes (J-shape, C-shape, etc.). Similarly, the bottom of the cavity 30A is flat as far as the exit, in other words does not incorporate oblique flats to initiate rolling. The width of the cavity 30A on the exit side is sufficient to allow the lens to pass freely.

The cassette 20 is fitted with a removable device 90 for immobilizing the lens 10. This device comprises an arm 91 having at a distal end an abutment 92 adapted to cooperate with the periphery of the optic part and/or one of the haptic members of the intraocular lens, to prevent inadvertent escape of the lens from the cassette. The arm 91 has at its proximal end, on the side of the exit from the cavity 30A, a hook 93 whose shape is substantially complementary to that of a tongue 94 on the base 21. In the immobilizing position, the hook 93 is interengaged with the tongue 94. In this position, the abutment 92 is able to cooperate with the haptic member near the exit and/or the peripheral edge of the optic part. As shown here, for an implant with three apertured flat haptic parts, the abutment enters for this purpose into the aperture in the optic [sic] member. The abutment 92 passes through a hole in the base perpendicular to the general plane of the bottom of the cavity 30A and constitutes a pivot allowing the arm 91 to pivot in the direction of the arrow from the immobilizing position toward a position in which the hook 93 passes over the tongue and toward the position shown in dashed outline, in which the abutment 92 may be withdrawn from the hole to release the intraocular lens (which is also shown in dashed outline).

Finally, note that one hook 27A is offset under the edge 26 and therefore next to the tongue 94. The function of the pair of hooks 27, 27A is exactly the same as that of the pair of hooks 27 in the first embodiment.

Obviously the cassette from FIGS. 1, 2 and 6 to 8, with a T-shaped cavity, may be provided with an immobilizing device of the above kind to improve retention of the intraocular lens in said cavity during sterilization and storage.

Before sterilization, the cassette containing the implant is placed in a flask (not shown) made from PPT polypropylene and filled with an appropriate saline solution and then hermetically sealed by a film. Thanks to the openings on the entry and exit sides, the aqueous solution can circulate inside the cassette and around the implant during the sterilization cycle. The presence of the aqueous solution inside the cavity 30, 31 prevents deterioration of the implant, and in particular of the haptic part, in the event of slight movement of the implant inside the cavity, whether in the direction of the optic axis of the implant or in the circumferential direction.

Autoclave sterilization is effected at approximately 120° C., and preferably at 121° C., for approximately 30 minutes, and generally in accordance with a technique known in the art. Once sterilized, the cassette and the implant have a shelf life of approximately two to five years.

Sterilization by gamma radiation in a saline solution to destroy micro-organisms is effected at a dose of approximately 25 kGy, using a technique known in the art. This is a preferential dose conforming to the French and European pharmacopoeia. Other doses, for example 35 kGy, conforming to the Danish pharmacopoeia, may equally be used. After sterilization, the cassette and the implant again have a shelf life of two to five years. According to one particularly advantageous protocol, the injector is sterilized at the same time as the cassette and the lens. To this end, the cassette with its lens and the injector are placed in a sealed flask filled with saline solution and then closed by a heat-sealed film.

Bimaterial implants made from flexible and rigid material, in particular from polymethylmethacrylate (PMMA) and hydrophilic acrylic, are described in PCT patent application WO99/65422. The flexible material is obtained from statistical methacrylate copolymers of methylmethacrylate hydroxyethylmethacrylate (MMA-HEMA) cross-linked by adding a multifunctional agent such as diethyleneglycol dimethacrylate. The rigid material of the lens is preferably based on PMMA-HEMA copolymers cross-linked by diethyleneglycol dimethacrylate. A bimaterial implant of this kind must be sterilized by gamma radiation to prevent opacification or chemical adulteration of the PMMA.

Finally, in the case of implants made from hydrophobic acrylic or silicone, the cassette is preferably made from ULTEM 1010F from General Electric, or from Hostalen PPT 1070 Si polypropylene from Hoechst, or from Riblene PE low-density polyethylene. The implant enclosed in its cassette is packaged in a container such as a blister pack with a film permeable to ethylene oxide and sterilized dry in a chamber with ethylene oxide, using a technique known in the art. Sterilization is followed by an aeration phase of about two weeks for desorption and evacuation of the gases. Implants of this kind have a shelf life in their cassette of two to five years, depending on circumstances.

Where necessary, other sterilization methods may be used, such as low-temperature plasma sterilization with hydrogen peroxide. An electromagnetic discharge generates free radicals that destroy the organic bonds of the micro-organisms. In this case, the cassette may be made from Ultem 1010F polyetherimide, Hostatel PPT 1070 polypropylene, or Riblene PE low-density polyethylene.

At the time of use, the cassette is removed from the flask or other container, where applicable with the injection device, if they are sterilized together in the same flask, and inserted directly into the housing of the injection device, as shown in FIGS. 3 to 6.

The injection device or injector 40 is of the syringe type and comprises a piston 60, a tubular body 50, and an implant ejection canula 70. The piston and the tubular body are separate components. The canula is preferably mounted in a removable manner at the exit 56 from the tubular body. Alternatively, the canula may be fastened to the tubular body at the exit 56. The piston 60 includes a cruciform guide member 61 whose width is substantially the same as the inside diameter of the bore 52 in the tubular body 50. The guide member is extended by a plunger 62 with a small diameter, of the order of 0.75 to 1.5 mm, and preferably 1.0 mm, small enough to limit the risk of the implant being wedged between the plunger and the cassette or between the plunger and the canula or end-piece. The plunger 62 has at the end a diametral groove 64 adapted to cooperate with the periphery of the optic part of the implant or where applicable with one of the haptic parts thereof, to advance it as far as the exit of the canula 70. The head 65 of the piston limits the forward movement of the plunger relative to the exit of the canula.

The bore 52 in the tubular body 50 has at its front end a frustoconical surface having the same cone angle as the first region at the entry of the cassette and continuous therewith and also serves to guide the distal end of the plunger of the piston 60. Beyond this frustoconical surface, and in communication therewith, is a transverse passage passing through the tubular body 50 and constituting a housing 53 for the cassette 20, and therefore having a longitudinal section complementary to the corresponding section of the cassette. This housing includes a guide groove 58 complementary to the guide rib 29 along the front of the lid 22 of the cassette 20. When the cassette 20 is inserted into the housing 53, it is retained by the hooks 27 and by the abutment 28. The cassette and/or the housing may be provided with means preventing the extraction of the cassette and thus preventing re-use of the cassette or the injector. There is a flange 57 on the exterior of the tubular body 50 at approximately one third of the distance from the proximal end of the body 50.

After loading the cassette 20 containing the intraocular lens 10 into the housing 53 in the tubular body 50, the piston may be inserted and advanced in the bore 52, through the frustoconical area at its front end and the frustoconical area at the entry of the cassette, and then come into contact through its groove 64 whose width is greater than the corresponding thickness of the engagement area of the optic part or, where applicable, that of one of the haptic members, to guide and drive the implant across the oblique flats 36 of the cassette constituting a ramp that progressively raises the implant from a plane parallel to the bottom of the cavity 30 in the base toward the general plane passing through the longitudinal axis of the canula. Raising the implant in this way defines a preferred rolling direction, here with the lateral haptic members passing over the haptic part. Rolling as such does not begin until the entry of the canula is reached, as shown in FIG. 8, in which the optic part may be seen to be slightly curved, thus beginning rolling. On the other hand, in the variant shown in FIG. 9, in which the cavity has a flat bottom, rolling is not started within the cavity.

The rolling process continues as the implant advances into the first portion of the canula 70, having the shape of a neck and reducing in size toward a second cylindrical portion of the canula, at whose distal end is the exit from the canula and thus the exit from the injection device as a whole. During this advance movement of the lens inside the neck, the implant rolls up on itself, progressively tightening around a diametral line of the optic part until the cylindrical portion reaches the exit from the canula 70. The circumferential rolling angle at the end of travel is greater than 360° and in practice approximately 540°. The exit is slightly oblique to facilitate ejection of the implant. The groove 64 on the plunger 62 then drives the implant to the exit from the canula, where it may unroll itself in the segment of the eye selected for implantation of the implant, i.e. the anterior chamber, the ciliary sulcus, or the capsular sac of the posterior chamber, as appropriate.

The components of the injection device 40 are preferably made from polypropylene or low-density polyethylene and may also be sterilized with ethylene oxide in a blister pack having a film permeable to this gas, under the usual conditions. In this case, the three components of the injector, i.e. the piston, the tubular body, and the canula, may be packaged in a single blister pack. To increase the shelf life of the tubular body and the piston to a value of from two to five years, the canula is then a component separate from the tubular body and packaged in an independent blister pack, with an earlier expiry date (approximately six months).

Obviously the present invention is not limited to the embodiments described or to the preferred materials, and to the contrary encompasses any variants in terms of structure, configuration and materials compatible with the objects of the present invention.

The invention claimed is:

1. An intraocular lens cassette for a lens injector of the type comprising a tubular body and a piston mobile in the tubular body to advance a lens toward an injection canula, the cassette being configured to be loaded into the tubular body and comprising a housing having a cavity configured for accommodating an intraocular lens in a rest position, an entry region for the piston, and an exit region for the lens, the cassette defining packaging for sterilizing the intraocular lens in situ, the cassette being held in a closed position when the housing encloses the lens, further comprising a releasable abutment for restraining the lens against movement in the housing in the closed position, the releasable abutment being cooperable with a haptic member or a periphery of an optic part of an intraocular lens for restraining the intraocular lens against movement, said releasable abutment member being movable into or out of a path of movement of a lens for injection.

2. The cassette according to claim 1, comprising a first cassette part and a second cassette part mounted for movement on the first cassette part between an open position and the closed position.

3. The cassette according to claim 2, comprising a releasable clip for holding the cassette in the closed position.

4. The cassette according to claim 1, comprising a releasable clip for holding the cassette in the closed position.

5. The cassette according to claim 1, wherein the housing is held permanently closed.

6. The cassette according to claim 1, for packaging a hydrophilic acrylic intraocular lens, wherein the cassette is made from a material sterilizable by autoclaving.

7. The cassette according to claim 6, wherein the cassette is made from polyetherimide resin.

8. The cassette according to claim 1, for packaging a bimaterial lens made from a hydrophilic flexible material and a rigid material, the cassette being made from a material sterilizable by gamma radiation.

9. The cassette according to claim 1, for packaging a lens made of hydrophilic flexible acrylic, wherein the cassette is made from a material sterilizable by gamma radiation.

10. The cassette according to claim 1, for packaging a lens made of silicone or a bimaterial lens made of a hydrophobic flexible acrylic and a rigid material or a hydrophobic acrylic, wherein the cassette is made from a material sterilizable by ethylene oxide.

11. The cassette according to claim 1, wherein the cassette is attachable to the tubular body.

12. The cassette according to claim 1, wherein an abutment limits the insertion of the cassette into the tubular body.

13. The cassette according to claim 1, wherein the cassette containing the intraocular lens made of hydrophilic acrylic is packaged in an autoclaving flask, the flask containing an aqueous solution and being hermetically sealed.

14. The cassette according to claim 1, wherein the cassette containing the intraocular lens made of hydrophilic acrylic is packaged in a flask for gamma radiation sterilization of the lens, the flask containing an aqueous solution and being hermetically sealed.

15. The cassette according to claim 1, wherein the cassette containing the intraocular lens which is made of silicon or hydrophobic acrylic is packaged in a hermetically sealed container.

16. The cassette according to claim 1, where the releasable abutment is connected to an arm having a hook that cooperates with a portion of the cassette in a lens restraining position.

17. Intraocular implant injector in combination with a cassette for accommodating an intraocular lens, comprising a tubular body and a piston mobile in the tubular body along a piston pathway between a stand-by position and an injection position, the injector having a canula disposed at an end of the tubular body opposite the piston, the tubular body defining a housing for receiving the cassette, the cassette defining a cavity for accommodating the lens in a rest position therein and aligned with the piston pathway of the piston and the injection canula, the cassette having an entry region for the piston and an exit region for the lens, the cassette defining packaging for sterilizing the intraocular lens in situ, the cassette being held in a closed position when the housing encloses the lens, a releasable abutment for restraining the lens against movement in the housing in the closed position, the releasable abutment being cooperable with a haptic member or a periphery of an optic part of an intraocular lens for restraining the intraocular lens against movement, said releasable abutment member being movable into or out of a path of movement of a lens for injection.

18. The injector according to claim 17, wherein the housing for receiving the cassette has a closed contour and comprises a slideway extending transversely to an axis of the tubular body and the piston.

19. The injector according to claim 18, wherein the slideway has a single cassette entry side, and the cassette is attached to the tubular body on a side opposite the entry side when the cassette is in place in the housing of the tubular body.

20. The injector according to claim 18, wherein an abutment limits the insertion of the cassette into the housing and cooperates with the tubular body on the entry thereof.

21. The injector according to claim 18, wherein the tubular body and the piston are made from a material sterilizable by ethylene oxide and are packaged together.

22. The injector according to claim 21, wherein the canula has a lubricant on a passage thereof and is packaged in packaging separate from the packaging for the tubular body and the piston and also separate from packaging for the cassette containing the intraocular lens.

23. The injector according to claim 18, wherein the canula is permanently fixed to the tubular body.

24. A method for packaging and loading an intraocular lens in an injector comprising the following steps:
  providing an intraocular lens and a cassette for accommodating the intraocular lens, the cassette having a piston entry region and a lens exit region, and a releasable abutment cooperable with a haptic member or a periphery of an optic part of an intraocular lens for restraining the intraocular lens against movement;
  enclosing the intraocular lens in a rest position inside the cassette;
  maintaining the cassette accommodating the intraocular lens closed, and sterilizing the intraocular lens inside the cassette;
  sterilizing the injector;
  inserting the cassette enclosing the lens into the injector with the piston entry region aligned therewith; and
  taking the releasable abutment out of a path of movement of the intraocular lens before injecting the lens into an eye.

25. The method according to claim 24, wherein the cassette is introduced into a hermetically sealed flask containing an aqueous solution, and the cassette accommodating the lens is autoclaved.

26. The method according to claim 24, wherein the cassette is introduced into a hermetically sealed flask containing an aqueous solution, and the lens accommodated in the cassette is sterilized by gamma radiation.

27. The method according to claim 26, wherein the injector is also introduced into the flask containing the aqueous solution for concomitant sterilization of the cassette and the injector.

28. The method according to claim 27, wherein the cassette is loaded into the injector before they are introduced into the flask containing the aqueous solution.

29. The method according to claim 25, wherein the injector including an injection canula are sterilized and packaged independently of the cassette and the lens.

30. The method according to claim 26, wherein the injector including an injection canula are sterilized and packaged independently of the cassette and the lens.

31. The method according to claim 29, wherein the injection canula is packaged separately from the cassette and the lens and the injector without the injection canula.

32. The method according to claim 30, wherein the injection canula is packaged separately from the cassette and the lens and the injector without the injection canula.

33. The method according to claim 24, wherein the cassette is inserted into the tubular body by sliding it in a transverse slideway in the tubular body and the cassette is clipped into place in the fully inserted position of the cassette in the tubular body.

* * * * *